(12) United States Patent
Kurtz

(10) Patent No.: US 9,474,613 B2
(45) Date of Patent: Oct. 25, 2016

(54) ACETABULAR FIXATION SYSTEM AND METHOD

(71) Applicant: William B. Kurtz, Nashville, TN (US)

(72) Inventor: William B. Kurtz, Nashville, TN (US)

( * ) Notice: Subject to any disclaimer, the term of this patent is extended or adjusted under 35 U.S.C. 154(b) by 23 days.

(21) Appl. No.: 14/210,437

(22) Filed: Mar. 14, 2014

(65) Prior Publication Data

US 2014/0277558 A1    Sep. 18, 2014

Related U.S. Application Data

(60) Provisional application No. 61/784,171, filed on Mar. 14, 2013.

(51) Int. Cl.
| | | |
|---|---|---|
| *A61F 2/32* | (2006.01) | |
| *A61F 2/34* | (2006.01) | |
| *A61F 2/46* | (2006.01) | |
| *A61B 17/04* | (2006.01) | |
| *A61F 2/30* | (2006.01) | |
| *A61B 17/84* | (2006.01) | |
| *A61B 17/17* | (2006.01) | |

(52) U.S. Cl.
CPC ............. *A61F 2/34* (2013.01); *A61B 17/0401* (2013.01); *A61F 2/4609* (2013.01); *A61B 17/1746* (2013.01); *A61B 17/842* (2013.01); *A61B 2017/0404* (2013.01); *A61F 2/30749* (2013.01); *A61F 2002/30462* (2013.01); *A61F 2002/30515* (2013.01); *A61F 2002/30772* (2013.01); *A61F 2002/3404* (2013.01); *A61F 2002/4662* (2013.01)

(58) Field of Classification Search
CPC .......... A61B 17/0401; A61B 17/1746; A61B 17/842; A61B 17/0404; A61F 2/34; A61F 2002/30462; A61F 2002/30515; A61F 2002/30749

See application file for complete search history.

(56) References Cited

U.S. PATENT DOCUMENTS

| | | | | |
|---|---|---|---|---|
| 2007/0142921 A1* | 6/2007 | Lewis et al. | ............... | 623/22.36 |
| 2012/0101588 A1* | 4/2012 | Forsell | ....................... | A61F 2/32 623/22.15 |
| 2013/0123841 A1* | 5/2013 | Lyon | ............................ | 606/232 |

* cited by examiner

*Primary Examiner* — Brian Dukert
(74) *Attorney, Agent, or Firm* — Brainspark Associates, LLC

(57) ABSTRACT

Improved methods, devices, systems and models for facilitating supplemental fixation of implant components to surrounding anatomical features, including supplemental fixation of acetabular components to the acetabulum.

17 Claims, 11 Drawing Sheets

ACETABULAR FIXATION SYSTEM AND METHOD

CROSS-REFERENCE TO RELATED APPLICATIONS

This application claims the benefit of U.S. Provisional Patent Application Ser. No. 61/784,171 entitled "Acetabular Fixation System and Method," filed Mar. 14, 2013, the disclosure of which is hereby incorporated by reference in its entirety.

TECHNICAL FIELD

The invention relates to improved orthopedic implants, as well as related methods, designs, systems and models. More specifically, disclosed herein are improved methods, designs and/or systems for joint implant components that facilitate supplemental fixation of an acetabular component to the acetabular bone.

BACKGROUND OF THE INVENTION

Acetabular components are typically implanted into the acetabular bone in a press fit manner and primarily rely on the ingrowth of bone onto the porous outer surface of the acetabular component. Alternative fixation between the acetabular component and the acetabular bone is possible with multiple different types of screw and peg options. Multiple different types of porous outer surfaces exist to improve the fixation of the acetabular component to the bone as well.

Most acetabular components typically have an opening at their apex (epicenter) of the hemisphere. This opening has a threaded screw hole so that the acetabular component can accept the threads on an acetabular impaction handle. This screw hole is typically located at the apex because the force generated from the mallet impacting the impaction handle is desirably directed in line with the opening of the acetabular component so the component does not change orientation of the opening of the acetabular component. The impaction force is desirably a true compression force that does not create a rotation moment as the acetabular component enters the prepared hemisphere in the acetabular bone. For the same reason that it is beneficial for the impaction force to be directed at the apex of the hemisphere, it is also beneficial for any alternative fixation devices to also direct their force in line with the apex of the hemisphere.

This opening in the acetabular component is sometimes closed with a dome screw cap or cover at the end of the case to prevent the fluid from inside the acetabular component from entering the bone over the 20 to 30 year life span of the implant. Joint fluid can carry polyethylene debris that encourages osteolysis.

Most alternative fixation devices rely on a screw obtaining purchase in the acetabular bone. These screw holes are located at different locations in the acetabular component. The screws are typically located 30 to 40 degrees away from the apex of the acetabular component. The screw holes are located in this position because surgeons typically want to advance screws into a substantial piece of acetabular bone and away from neurovascular structures. The thickness of acetabular bone is greatest in a superior direction, so most screws are positioned in a superior direction. The thickness of the bone located in the direction of the apex of the hemisphere can sometimes limit the amount of bone available to be purchased by a screw. Therefore, screws are often not used in the dome screw hole, but are generally used 30 to 40 degrees away from the apex where the bone is thicker. When the screw is some distance away from the apex, there can be a compression stress between the acetabular bone and acetabular component at the screw location, but a tensile stress on the opposite side of the acetabular component from the moment that is generated by obtaining fixation on just one side of the component. This tensile stress can lead to micro-motion of the acetabular component, failure of acetabular component in-growth and possibly loosening of the acetabular component.

The joint reactive force in an acetabular component is typically directed in a mostly superior and slightly medial direction as the patient's body weight pushes down and the prosthetic hip pushes up. This superior directed force can cause a moment force of the acetabular component that causes a compressive force superiorly and a tensile force medially. The superior directed screw is not ideally positioned to resist this moment force. A medially directed screw would be better positioned to resist this moment force, but the thickness of bone medially prevents adequate screw purchase in most situations.

Alternative fixation between the acetabular component and the acetabular bone is increasingly important in acetabular revision surgery. When a patient has had an acetabular component implanted and then later removed, the acetabular bone is generally less receptive to another acetabular component. Obtaining adequate initial acetabular component fixation is more difficult in a revision setting, and surgeons often have to rely on these alternative fixation devices. Surgeons will often implant multiple screws through the many screw holes in the acetabular component into multiple locations of the acetabular bone.

Various surgical devices in the past have sought to obtain additional fixation between the acetabular component and acetabular bone, but these devices have various limitations. See, for example, the devices disclosed in U.S. Pat. No. 2,765,787 filed on Aug. 2, 1954, U.S. Pat. No. 5,549,691 filed on Feb. 3, 1994, U.S. patent application Ser. No. 20070142921 filed Dec. 21, 2005 and U.S. patent application Ser. No. 20070142922, filed Dec. 21, 2005.

BRIEF SUMMARY OF THE INVENTION

Acetabular components can be attached to acetabular bone using a multitude of different devices, methods, systems and means. Various embodiments disclosed herein include the deployment of an endobutton through an existing hole in an acetabular component, through the acetabular bone, and to the inner table of the pelvic bone. The endobutton could be rotated to grab the inner table of the pelvic bone. A suture could then contract and/or draw the endobutton to the acetabular component, desirably creating considerable compression between the acetabular bone and acetabular component. The suture could be tightened in a variety of ways, including by using a mechanical advantage system like a gear mechanism, and the suture can be permanently secured to the acetabular component, such as by using a metal dome screw that could thread into the dome screw threads at the apex of the acetabular component.

BRIEF DESCRIPTION OF THE SEVERAL VIEWS OF THE DRAWINGS

The foregoing and other objects, aspects, features, and advantages of embodiments will become more apparent and may be better understood by referring to the following description, taken in conjunction with the accompanying drawings, in which.

DETAILED DESCRIPTION OF THE INVENTION

Figure 1A:
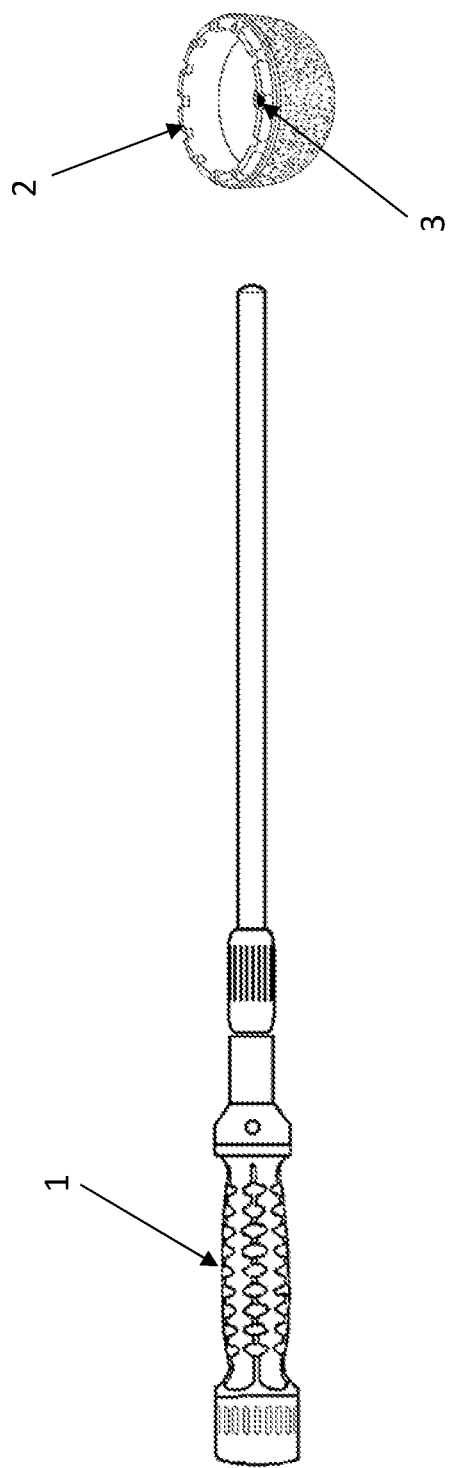
FIGS. 1a and 1b depict perspective views of one embodiment of an acetabular insertion handle and an acetabular component.
Figure 1B:
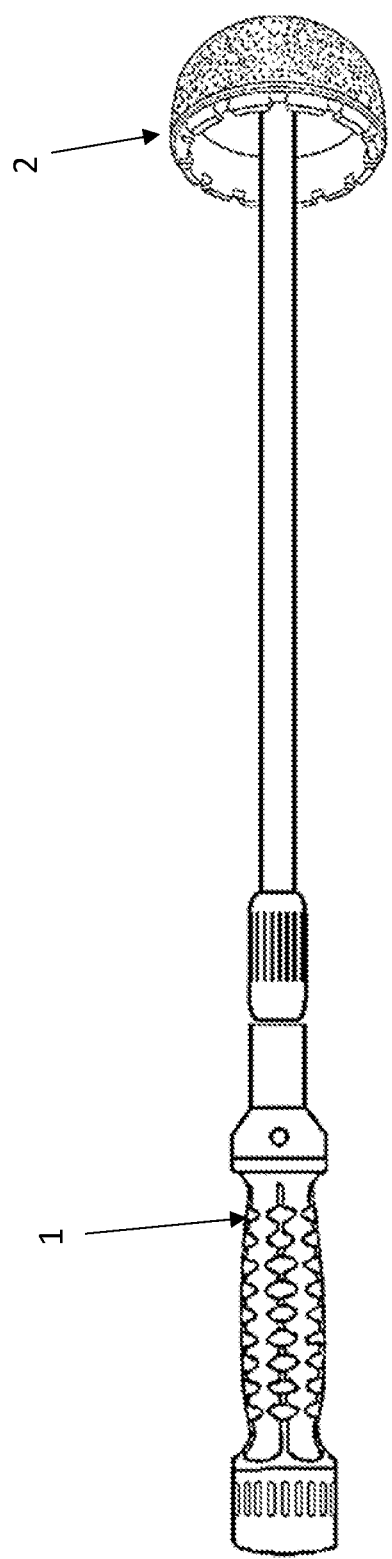

FIG. 1a depicts a perspective view of an acetabular insertion handle 1, an acetabular component 2 and a threaded dome screw hole 3 at the apex of the acetabular component. FIG. 1b depicts a perspective view of an acetabular insertion handle 1 attached to an acetabular component 2. The attachment can be via the threads in the dome screw hole.

In this embodiment of the invention, the acetabular insertion handle could be hollow along the center axis to accept a drill bit. The surgeon could impact the acetabular component into the acetabular bone and then drill through the insertion handle and into the acetabular bone. The drill bit and insertion could have a mechanical stop to prevent the surgeon from drilling too far into the patient's pelvis. This mechanical stop could be set to allow the surgeon to drill 10 mm at first. If the surgeon did not penetrate through the acetabular bone and into the inner pelvis, then the surgeon could set the mechanical stop at 15 mm and drill again. These steps could be repeated until the surgeon successfully and safely drilled through the acetabular bone or medial wall of the acetabulum. The drill bit could have a depth gauge on it or a separate depth gauge could be used and referenced off of the insertion handle.

Figure 2:
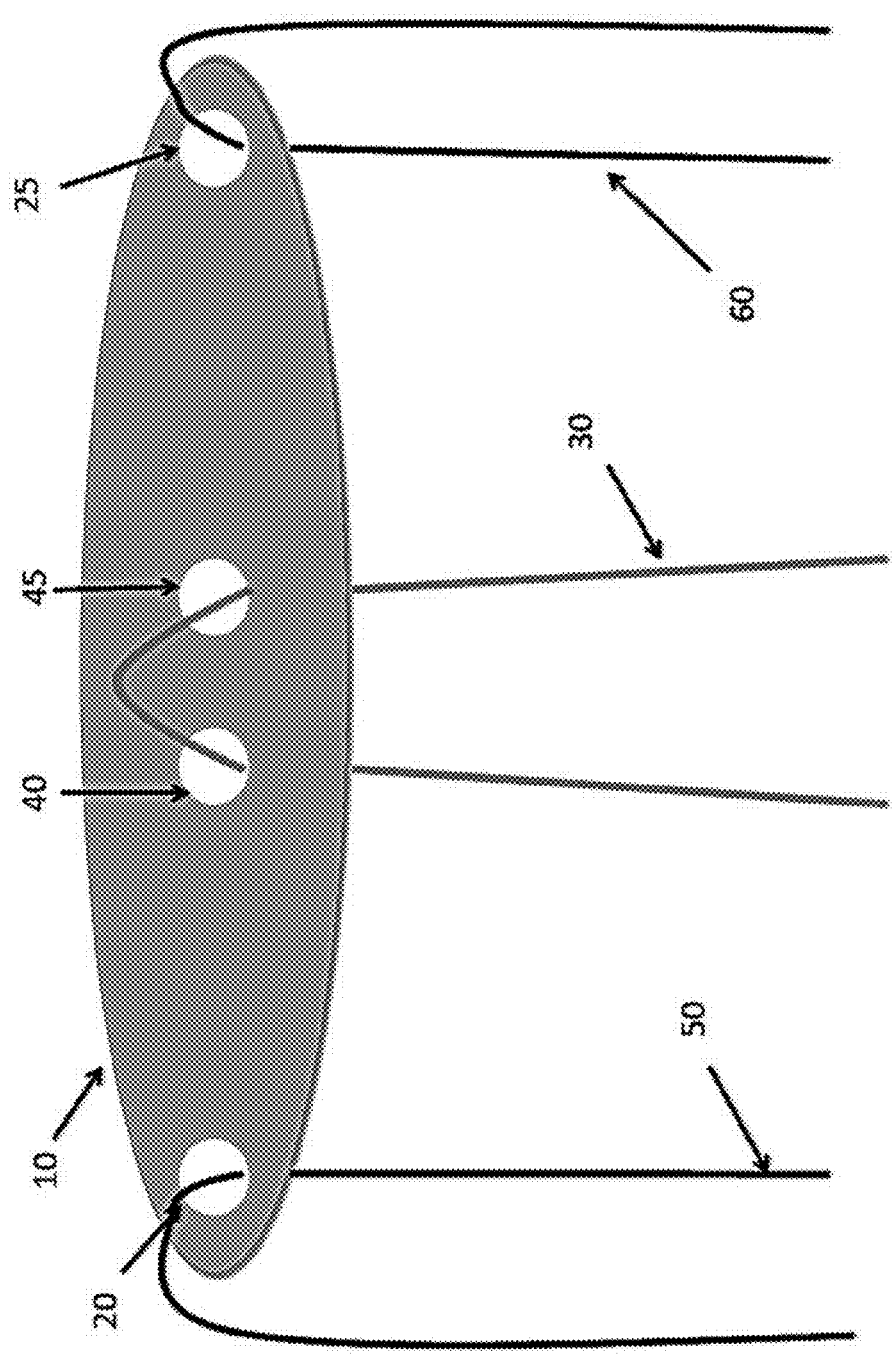
FIG. 2 depicts a front plan view of one embodiment of an endobutton securement device, showing the positioning sutures on either end of the endobutton and the central suture that could connect to the acetabular component.

FIG. 2 depicts a frontal view of one exemplary embodiment of an acetabular anchoring device or endobutton 10, showing various positioning sutures 50, 60 on either end of the endobutton and a tensioning suture 30 that could connect to the acetabular component (not shown). The positioning suture 50, 60 could loop through a hole 20, 25 in the endobutton and then over the edge of the endobutton. The tensioning suture 30 could loop through one hole 40 and back through the another hole 45.

The endobutton could have a narrow dimension and a long dimension so that the endobutton could be passed through a long tunnel in the bone and then flipped to gain purchase of the surface of the inner wall of the pelvis. The endobutton could be made from metal, polymer or any other material commonly used in surgeon. It could be permanent or absorbable.

The positioning sutures could loop around the ends of the endobutton and allow the surgeon to advance either one side or both sides together. The positioning suture could be made out of any material like nylon. If desired, the positioning suture could be removed at any point during the surgery, such as the middle of the operation, after the endobutton was positioned on the inner wall of the pelvis.

The tension suture could be any heavy-duty suture material (or other material) that could be designed and or appropriately sized to withstand considerable force. Exemplary materials can include Fiberwire, Mersilene tape, metal wire or other braided sutures, which are desirably non-exclusive examples of possible material that could be used.

Figure 3:
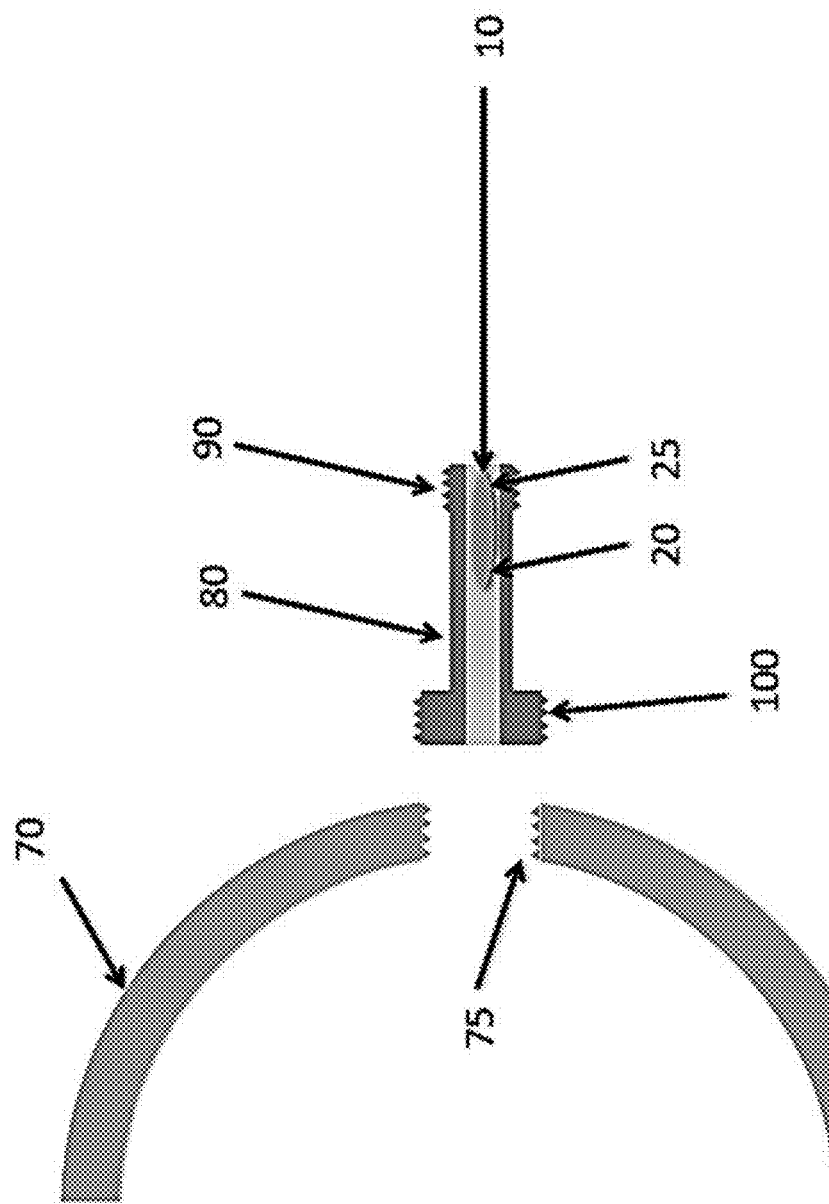
FIG. 3 depicts a cross-sectional view of an acetabular component, a dome screw, and an endobutton preloading inside the dome screw.

FIG. 3 depicts a cross sectional view of an acetabular component 70, a dome screw 80, and an endobutton 10 that has been preloaded inside of the dome screw 80. The dome screw could have screw threads 100 or other features that could attach to the screw threads 75 of the dome screw hole of acetabular component. The acetabular dome screw hole threads 75 could be the same screw threads used to accommodate the acetabular insertion handle. The dome screw could have screw threads 90 that engage the acetabular bone. The endobutton 10 is shown inside the hollow portion of the dome screw hole.

The dome screw could be made in multiple different lengths. The length of the screw needed and/or desired could be determined by the surgeon using a depth guide to measure the thickness of the medial wall acetabular bone as described above. The surgeon might want to use a dome screw somewhat shorter than the thickness of the bone to ensure adequate compression between the inner wall of the pelvis and the endobutton. The dome screw could be available with different threads to attach to different acetabular components.

The endobutton is shown preloaded in the dome screw, but could alternatively be packaged and inserted separately without the dome screw attached. The dome screw could then be inserted after the endobutton is flipped and secured to the inner wall of the pelvis.

Figure 4A:
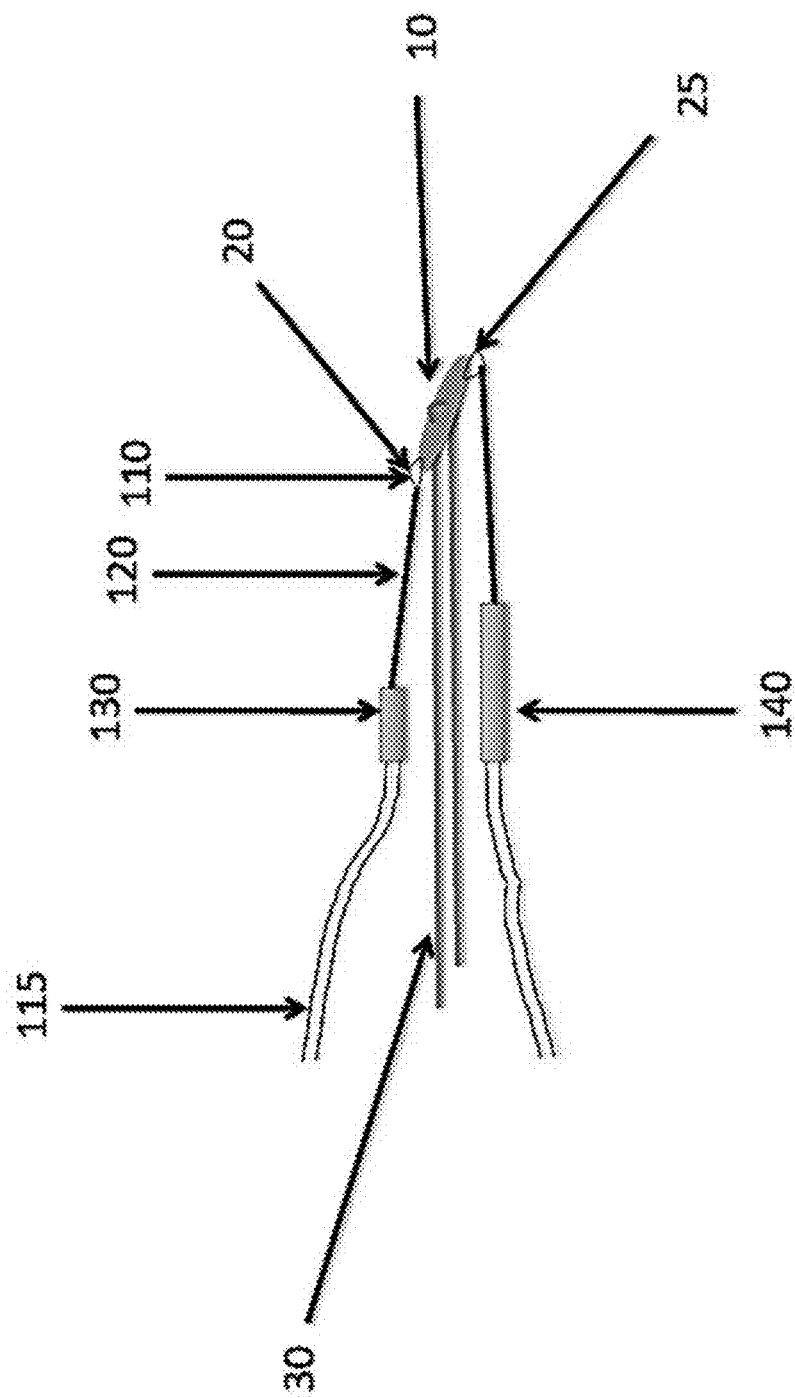
FIGS. 4a and 4b depict front plan views of exemplary positioning sutures that can be attached to the endobutton.
Figure 4B:
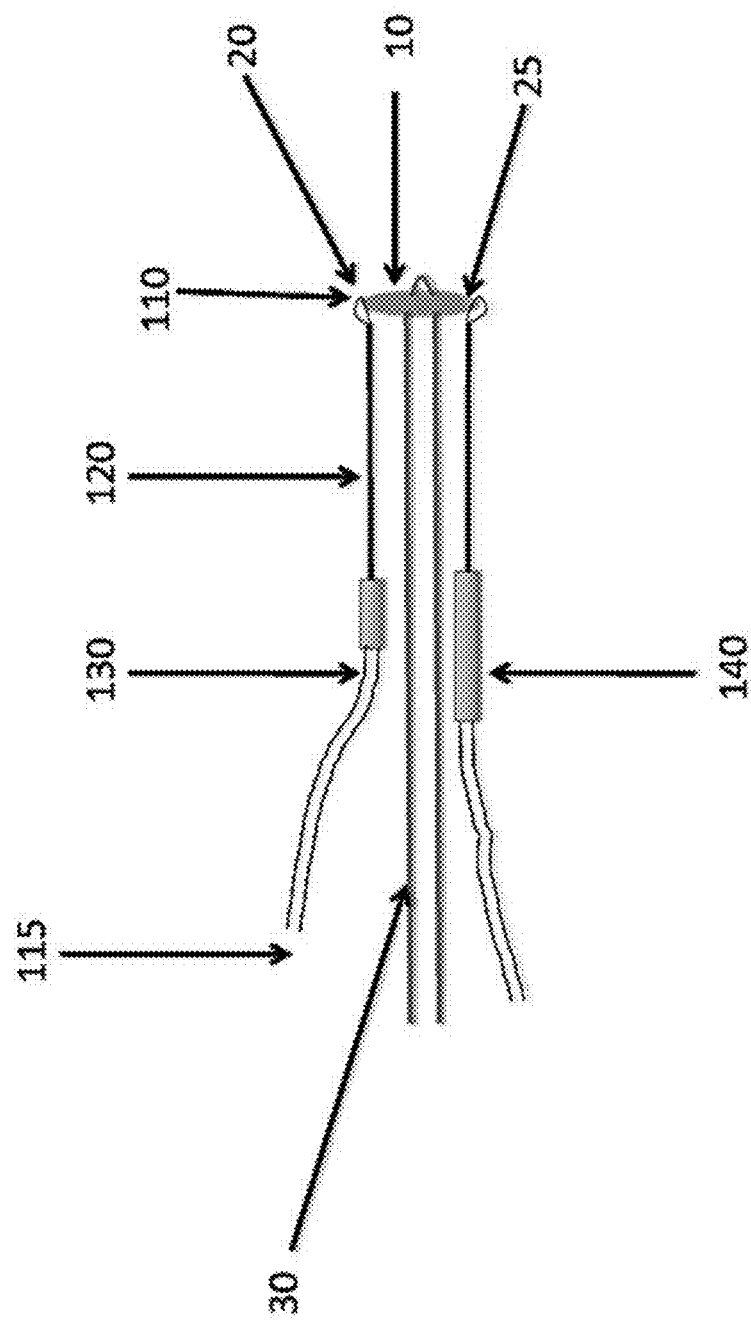

FIGS. 4a and 4b depict frontal views of the positioning sutures 110 attached to near end 20 and far end 25 of the endobutton 10, the tension sutures 30 attached to the endobutton 10, a cannulated metal sleeve 120 that houses the positioning suture 110, a short handle 130 that allows the surgeon to push and pull the near end of the endobutton through the metal sleeve and suture, a long handle 140 that allows the surgeon to push and pull the far end of the endobutton through the other metal sleeve and suture, and the positioning suture 115 exiting the handles.

The cannulated metal sleeve could act similar to a Huston suture passer. The positioning suture could pass through the handle, through the metal sleeve, through the hole in the endobutton, around the end of the endobutton, back into the metal sleeve, back through the handle and out the end of the handle. There could initially be some mild tension of the positioning suture to minimize the loop made at the endobutton end. The surgeon could push and pull on the handles to move the metal sleeve and thereby move each end of the endobutton independently. The metal sleeve could pass through the inner hollow portion of the dome screw and into the drill hole in the acetabular bone. The handles could therefore be able to push the endobutton through the hollow portion of the dome screw, through the drill hole in the acetabular bone, and out of the pelvic bone and into the inner pelvic cavity.

The two handles of the endobutton could be designed so that the far ends of the handles could initially be flush as shown in FIG. 4a. The short handle could be attached to the end of the endobutton that was closest to the acetabular component. The surgeon could initially advance both handles to the depth measured by the depth gauge during the bone drilling process. The measurement could correspond with the endobutton leaving the drill hole and passing the surface of the inner wall of the pelvis. The surgeon could then advance the short handle, to desirably advance just the end of the endobutton that was closest to the acetabular component until the opposite end of the two handles were flush, such as seen in FIG. 4b. The surgeon could then pull back on the tensioning suture or the positioning sutures to pull the endobutton flush with the inner wall of the pelvis.

The surgeon could remove the positioning suture by pulling on just one end of the positioning suture 115 as it exits the handle. The other end of the positioning suture could be pulled through the hole in the endobutton and back out of the metal sleeve. The removal of the positioning suture could be done before the surgeon tensioned the tensioning suture so that the positioning suture could move through the hole in the endobutton easier.

Figure 5:
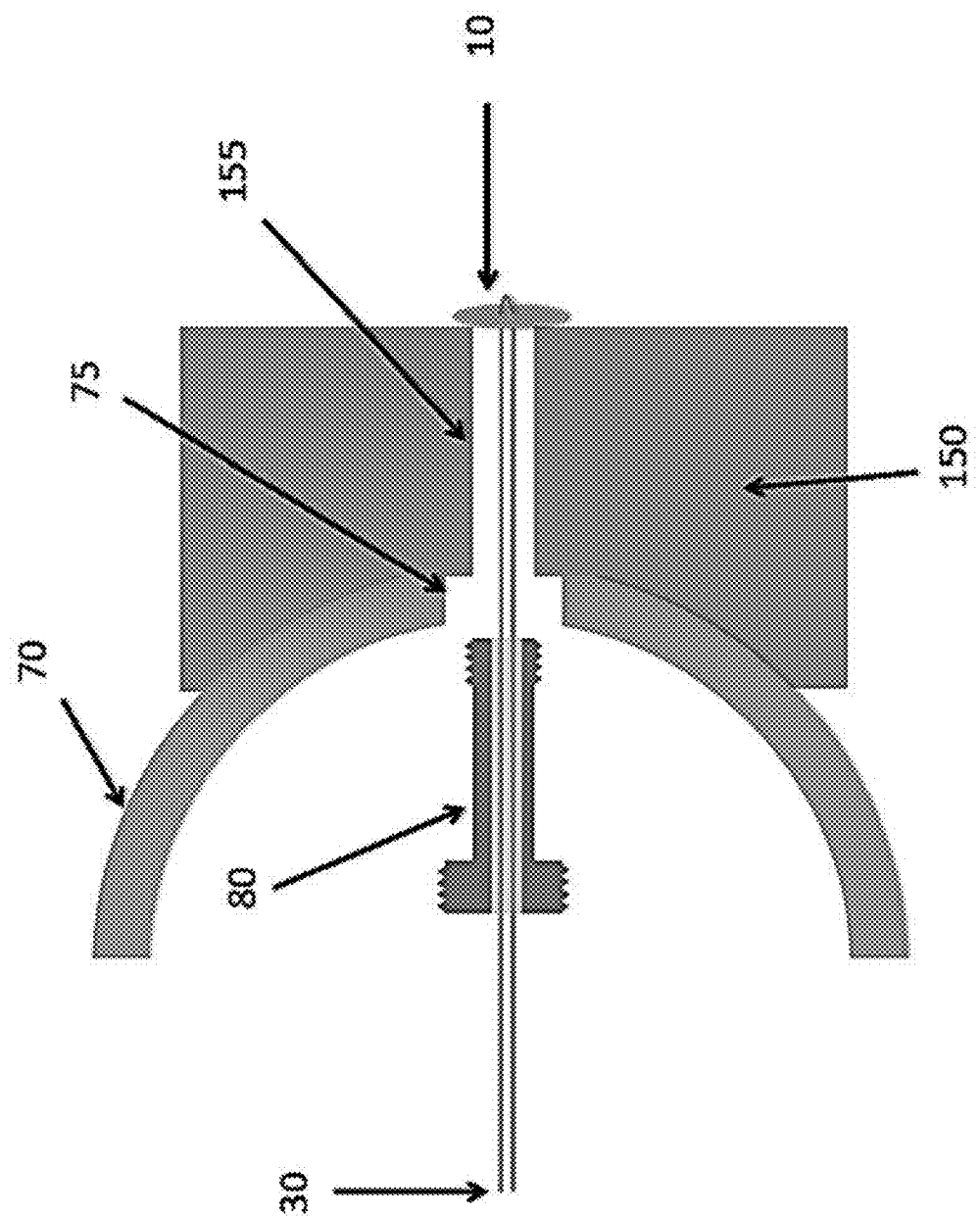
FIG. 5 depicts a cross-sectional view of an endobutton that is deployed on one side of a bone (i.e., an acetabulum), a suture attached to the endobutton, a component (i.e., an acetabular component) implanted in a bone (i.e., an acetabulum), and a dome screw.

FIG. 5 depicts an endobutton 10 on one side of a bone 150 (acetabulum), a tension suture 30 attached to the endobutton 10, an acetabular component 70 implanted in a bone 150 (acetabulum), a dome screw 80 that is to be inserted through the dome hole 75 in the acetabular component and into a drill hole 155 that has been made in the acetabular bone 150.

The surgical scenario shown in FIG. 5 may be particularly useful where the surgeon has inserted the acetabular component, drilled the drill hole in the acetabular bone, and chose to insert the endobutton separately from the dome screw. Once the endobutton has been inserted, flipped, and positioned on the inner wall appropriately, the surgeon could then insert the dome screw into the acetabular component and attach the tensioning suture to the dome screw.

Figure 6A:
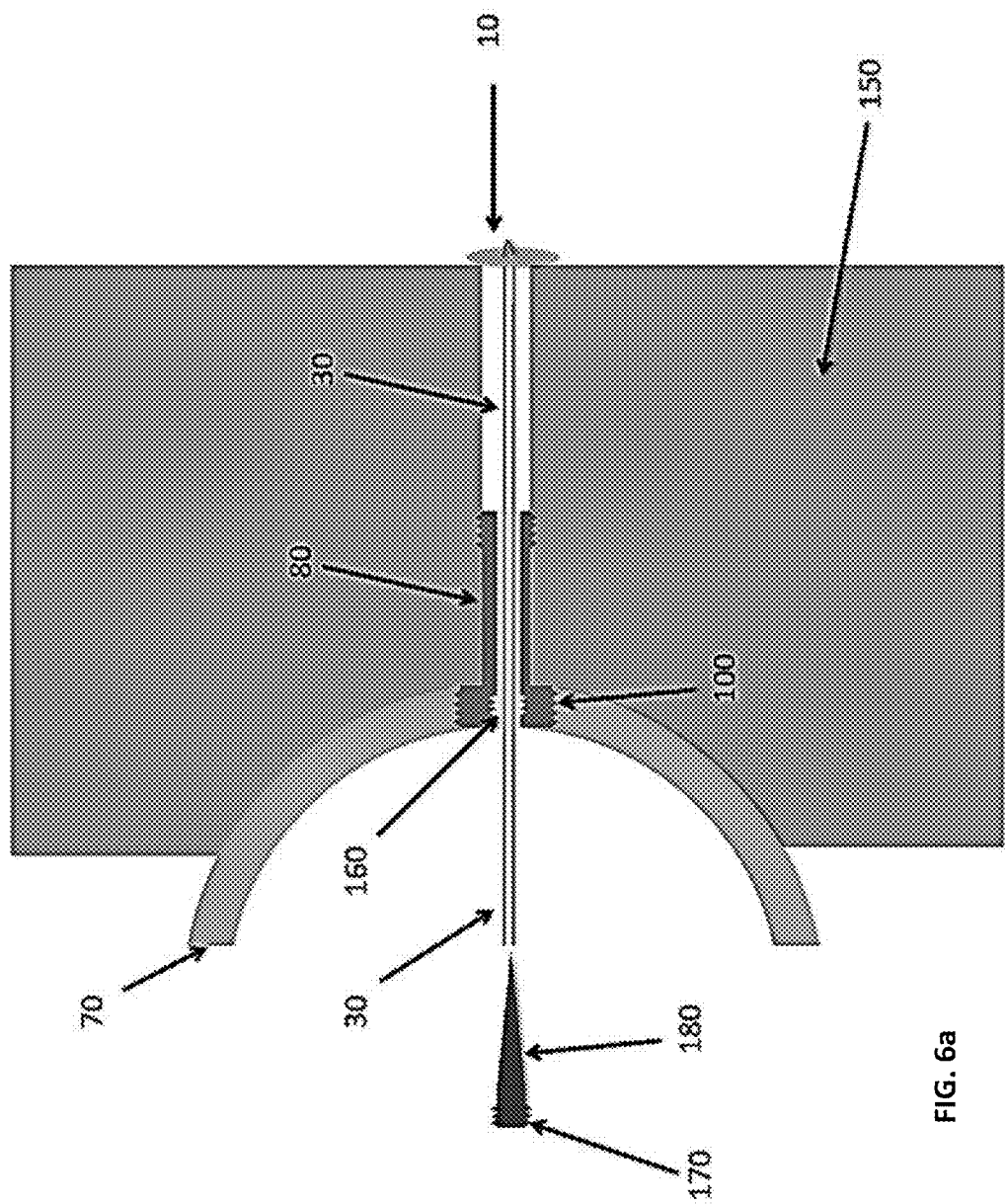
FIGS. 6a and 6b depict cross-sectional views of an endobutton on one side of a bone (acetabulum), a suture attached to the endobutton, a component (acetabular component) implanted in a bone (acetabulum), a dome screw attached to the component, and an interference screw.
Figure 6B:
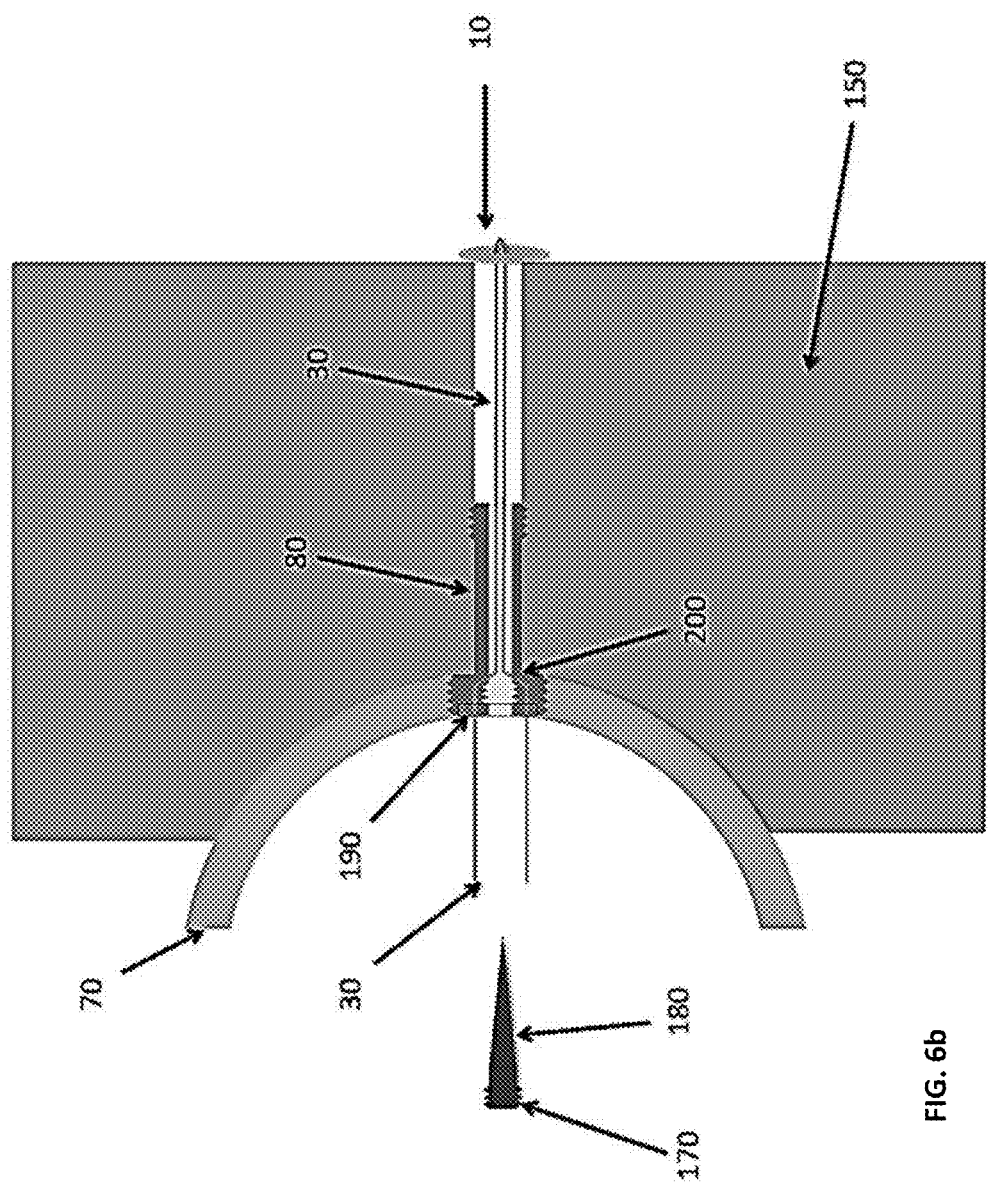

FIGS. 6a and 6b depict an endobutton 10 on one side of an acetabular bone 150, a tension suture 30 attached to the endobutton, an acetabular component 70 implanted on the opposite side of the acetabular bone from the endobutton, a dome screw 80 attached to the acetabular component via screw threads 100, an interference screw 180 shown outside of the dome screw, and screw threads of the interference screw 170 that can engage the inner screw threads 160 in the dome screw and secure fix the tension suture to the dome screw. FIG. 6b further depicts the tension sutures 30 bypassing in the inner screw threads 160 and running through a small channel 200 in the dome screw 80. FIG. 6b further depicts an indentation 190 in the screw head of the dome screw that could accept a large screwdriver 210 like a hex head screwdriver.

The surgical scenario shown in FIGS. 6a and 6b may be particularly useful where the surgeon has inserted the acetabular component, drilled through the acetabular bone and to the inner pelvis, inserted the dome screw, and then advanced the endobutton to the inner wall of the pelvis.

A screwdriver 210 that inserts the dome screw into the acetabular component could be hollow to allow it to house the positioning suture 110, the metal sleeves 120, and the short 130 and long 140 handles. The surgeon could use this screwdriver to thread the dome screw into the acetabular component and then immediately (if desired) advance the two ends of the endobutton as described above. The tensioning suture could run through the center hollow opening of the screwdriver. Gentle tension could be placed on the tensioning suture to ensure that the endobutton was properly positioned and the positioning suture 110 and the metal sleeves 120 could be removed from the hollow portion of the dome screw and the screwdriver. The tensioning suture could be attached to a mechanical gear inside the screwdriver. A part of the screwdriver could be turned or twisted to activate the gears and tighten the tensioning suture around a rotating gear or cylinder. Many arrangements of gearing or other similar systems of gears or other devices exist in orthopedics for tightening of cerclage wires around bones, which may be useful in conjunction with various features of the embodiments described herein. The interference screw could be inserted through the opening in the screwdriver and fastened to the inside of the dome screw (FIG. 7a) to dome screw and/or the interference screw could have some deformable part such as a small channel 200 that could be collapsed when the interference screw is threaded into the dome screw, desirably firmly attaching the tensioning suture to the dome screw. Alternative suture fixation methods are possible as well, including by tying the suture.

Figure 7A:
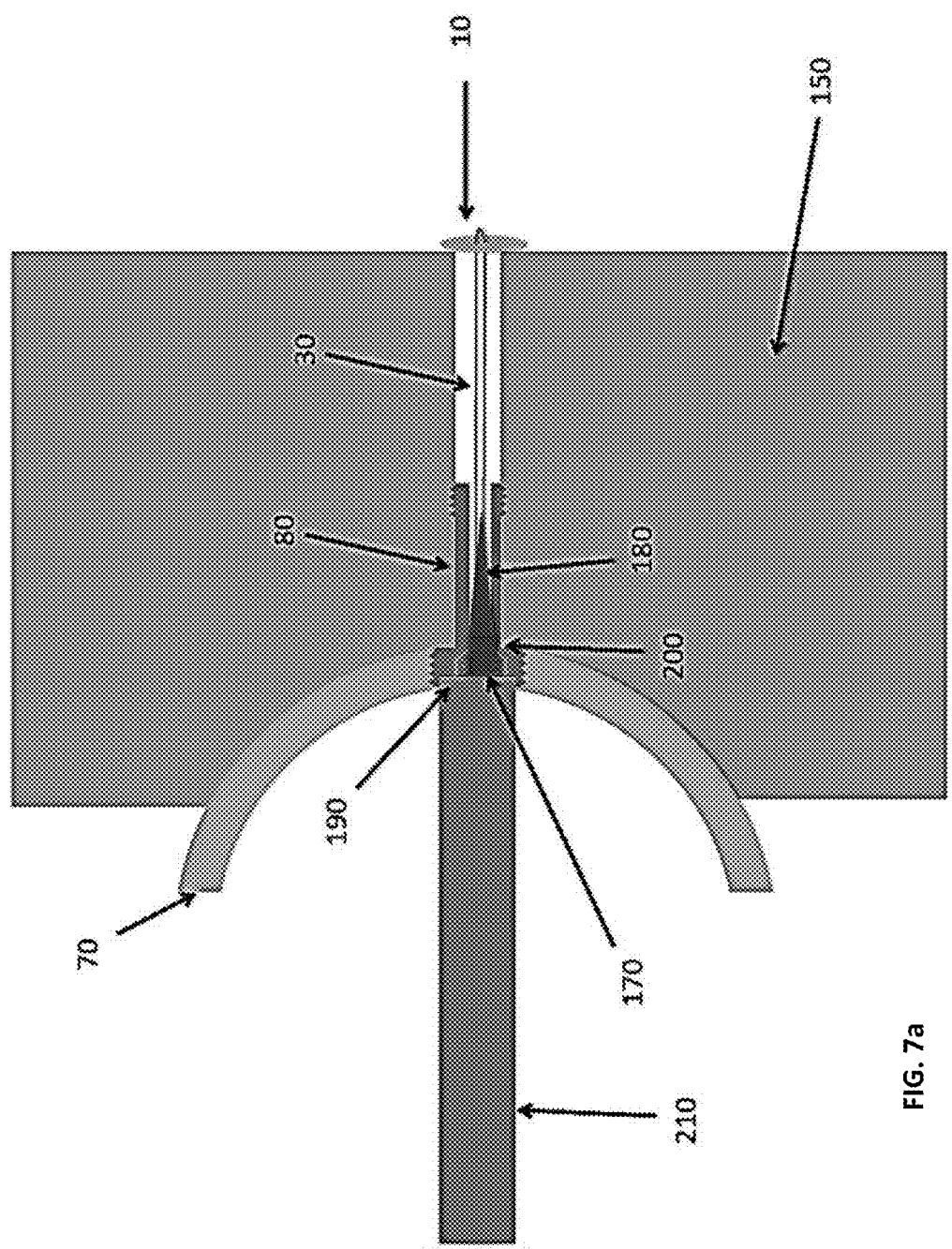
FIGS. 7a and 7b depict cross-sectional views of an endobutton on one side of a bone (acetabulum), a suture attached to the endobutton, a component (acetabular component) implanted in a bone (acetabulum), a dome screw attached to the component, an interference screw, and an interference screw engaging the suture and dome screw.

FIG. 7a depicts an endobutton 10 on one side of a bone (acetabulum), a tension suture 30 attached to the endobutton and the dome screw via the interference screw 180, an acetabular component 70 implanted in an acetabulum bone 150, a dome screw 80 attached to the acetabular component, an interference screw threads 170 engaging the inner dome screw threads, the tension suture secured to the dome screw by the interference screw before it runs through the channel in the dome screw 200, and the screwdriver attached to the dome screw. FIG. 7a shows an example of a final completed structure. In this embodiment, the interference screw has been advanced into the dome screw to securely attach the tension suture to the dome screw.

Figure 7B:
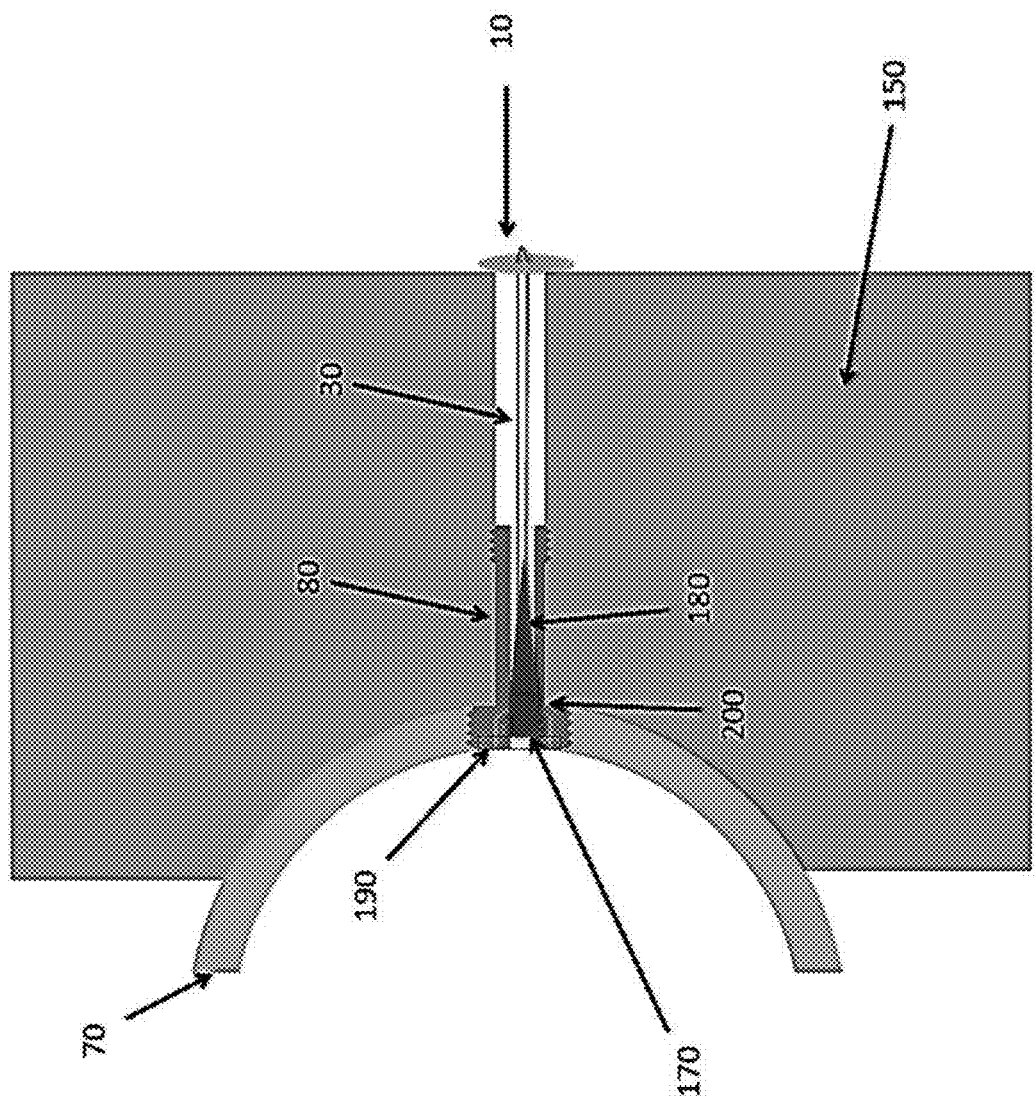

FIG. 7b depicts the final construct with the screwdriver removed and the tension suture cut at the face of the dome screw. Once the interference screw has been engaged and securely attached the tensioning suture to the dome screw, the tensioning suture could be detached from gear mechanism of the screwdriver, the screwdriver could be removed, and the tensioning sutures could be cut (if desired).

The screwdriver 210 could take on many shapes and sizes. The purposes of the screwdriver could include threading the dome screw into the acetabular component, allowing passage of the metal sleeves 120 that could allow the endobutton to flip, measuring of the distance that the handles 130 & 140 travel (and thus the distance that the two ends of the endobutton travel), tensioning the tensioning suture with some mechanical advantage through a gear or lever, and/or allowing the interference screw to be inserted while the tensioning suture had adequate tension. The screwdriver could remain attached to the dome screw through the whole deployment of the endobutton, if desired.

The screw threads in the dome screw and the screw threads in the acetabular component could engage to form a fixed angle device. The angle between the acetabular component and the dome screw could then be held constant and offer further fixation of the acetabular component to the acetabular bone.

The drawings and text above refer to the implantation of an acetabular component into an acetabular bone for descriptive purposes only. Similar principles as those described above could be applied to other joints like the knee, ankle, feet, shoulder, elbow, back and wrist.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. The scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein.

What is claimed is:

1. A method of securing an acetabular cup in a desired alignment to a patient's acetabular bone, comprising:
   inserting an acetabular component into a first drill hole that has been made in the patient's acetabular bone;
   accessing the patient's acetabular bone through an opening in the acetabular cup and drilling a second drill hole into the patient's acetabular bone;
   inserting an anchoring device through the opening in the acetabular cup and into the second drill hole, the anchoring device including a deployable anchoring element positioned within a lumen of the anchoring device, the deployable anchoring element including an attached flexible anchoring structure;
   deploying the deployable anchoring element out of the lumen to anchor the deployable anchoring element to the patient's acetabular bone by advancing the deployable anchoring element out through a distal end of the lumen and manipulating the attached flexible anchoring structure to reorient the deployable anchoring element such that the deployable anchoring element presents an enlarged cross-sectional area to the second drill hole, at least a portion of the attached flexible anchoring structure extending through the second drill hole and through at least a portion of the lumen of the anchoring device;
   tensioning the attached flexible anchoring structure, and connecting at least a portion of the attached flexible anchoring structure to the anchoring device.

2. The method of claim 1, wherein the anchoring device comprises a dome screw having a head and a shaft, and the head of the dome screw includes an outer diameter that is larger than an outer diameter of the shaft.

3. The method of claim 2 wherein the shaft includes a first longitudinal length, and the head includes a second longitudinal length, and the first longitudinal length is greater than the second longitudinal length.

4. The method of claim 2, wherein the opening in the acetabular cup has a bore depth, and a longitudinal length of the dome screw is greater than the bore depth.

5. The method of claim 2, wherein the attached flexible anchoring structure comprises a first suture, a second suture and a third suture.

6. The method of claim 5, wherein the first suture includes an alignment indicator.

7. The method of claim 2, wherein the dome screw further comprises a locking mechanism for securing the attached flexible structure to the dome screw.

8. The method of claim 1, wherein the anchoring device includes a proximal end and a distal end, and the deployable anchoring element is positioned within the lumen of the anchoring device adjacent the proximal end.

9. The method of claim 5, wherein the attached flexible anchoring structure includes an alignment indicator that reflects an alignment of the deployable anchoring element.

10. The method of claim 1, wherein the step of tensioning the attached flexible anchoring structure comprising tensioning the attached flexible anchoring structure using a mechanical advantage system.

11. The method of claim 1, wherein the opening in the acetabular cup is located at an apex of the acetabular cup.

12. The method of claim 2, wherein an exterior surface of the dome screw is threaded.

13. The method of claim 1, wherein an inwardly facing surface of the lumen is threaded.

14. The method of claim 2, wherein an upper surface of the dome screw includes an indentation for engaging a corresponding element of a driving tool.

15. The method of claim 1, wherein an exterior surface of the anchoring device is threaded.

16. The method of claim 1, wherein at least a portion of an outer surface of the acetabular cup comprises a porous material.

17. The method of claim 2, wherein the deployable anchoring element comprises an absorbable material.

* * * * *